United States Patent [19]

Stadler et al.

[11] 4,224,315
[45] Sep. 23, 1980

[54] PSEUDOTRISACCHARIDES AND THEIR MEDICINAL USE

[75] Inventors: Peter Stadler, Haan; Karl G. Metzger, Wuppertal; Uwe Petersen, Leverkusen; Eckart Voss, Cologne, all of Fed. Rep. of Germany

[73] Assignee: Bayer Aktiengesellschaft, Leverkusen, Fed. Rep. of Germany

[21] Appl. No.: 931,708

[22] Filed: Aug. 7, 1978

[30] Foreign Application Priority Data

Aug. 18, 1977 [DE] Fed. Rep. of Germany ....... 2737264

[51] Int. Cl.$^2$ .................. A61K 31/71; C07H 15/22
[52] U.S. Cl. ........................... 424/180; 536/17 R; 536/18
[58] Field of Search ................ 536/17; 424/180

[56] References Cited

U.S. PATENT DOCUMENTS

| | | | |
|---|---|---|---|
| 3,997,524 | 12/1976 | Nagabhushan | 536/17 |
| 4,044,123 | 8/1977 | Daniels et al. | 536/17 |
| 4,063,015 | 12/1977 | Mallams | 536/17 |

*Primary Examiner*—Johnnie R. Brown
*Attorney, Agent, or Firm*—Sprung, Felfe, Horn, Lynch & Kramer

[57] ABSTRACT

The invention includes, as novel compounds, aminoglycoside antibiotics of the 4,6-di-O-(aminoglycosyl)-1,3-diaminocyclitols which are 3-N″-substituted. Also included in the invention are compositions containing said novel compounds and methods for the use of said compounds and compositions.

32 Claims, No Drawings

PSEUDOTRISACCHARIDES AND THEIR MEDICINAL USE

The invention relates to new pseudotrisaccharides, processes for their preparation and their use as medicaments.

In particular, the invention relates to new, antibacterially active aminoglycoside antibiotics of the 4,6-di-O-(aminoglycosyl)-1,3-diaminocyclitol type.

Aminoglycoside antibiotics are important substances for effectively combating bacterial infections. However, in many cases the appearance of resistant germs decreases their wide applicability; furthermore, side-effects, such as, for example, ototoxicity and nephrotoxicity can occur.

The compounds according to the invention are pseudotrisaccharides of the following general formula (I) or their salts:

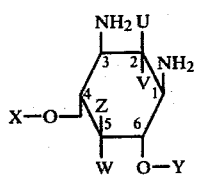

in which
X represents a radical of the formula

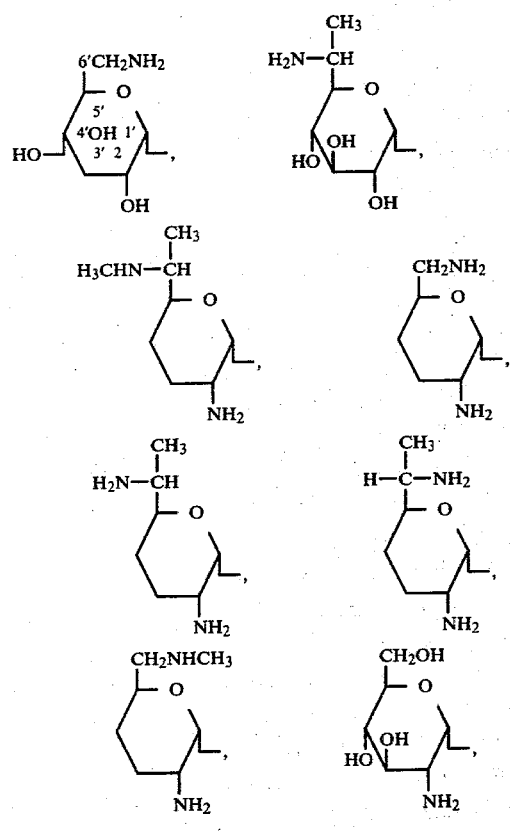

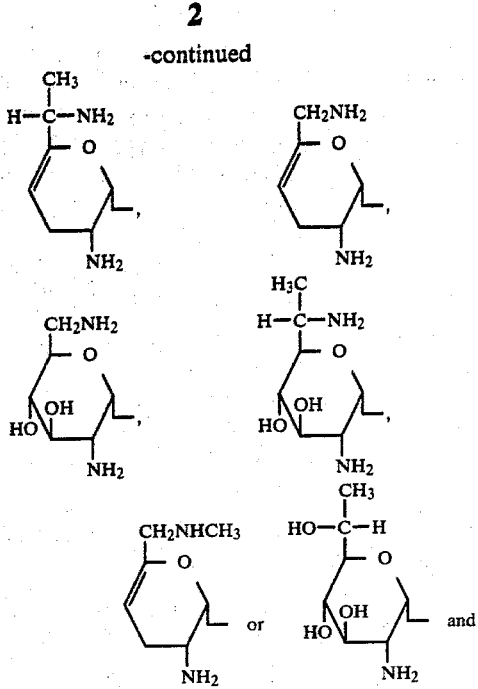

Y designates a radical of the formula

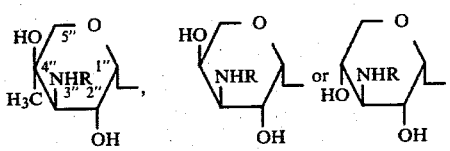

U, V and W are the same or different and each is hydrogen or hydroxyl,
Z is hydrogen, hydroxyl or amino, and
R is alkyl having at least 2 carbon atoms, alkenyl, alkinyl, cycloalkyl, cycloalkenyl, cycloalkylalkyl, cycloalkenylalkyl, aryl or aralkyl, each of the hydrocarbon radicals being optionally substituted.

Alkyl designates a straight-chain or branched alkyl radical having preferably from 2 to 8 carbon atoms, which can preferably carry from 1 to 3, in particular 1 or 2, identical or different substituents. Examples of substituents which may be mentioned are: hydroxyl, alkoxy with preferably from 1 to 4 carbon atoms, alkylthio with preferably from 1 to 4 carbon atoms, halogen, preferably fluorine, chlorine or bromine, nitro, amino and monoalkylamino and dialkylamino with preferably from 1 to 4 carbon atoms per alkyl group. Examples of alkyl radicals of the type mentioned are: ethyl, n-propyl, n-butyl, n-pentyl, n-heptyl, β-methylpropyl, t-butyl, β-propylpentyl, δ-ethylhexyl, β-dimethylpropyl, β-hydroxypropyl, β,γ-dihydroxypropyl, ε-hydroxypentyl, δ-hydroxybutyl, γ-hydroxypropyl, β-methoxyethyl, β-butoxyethyl, β-methoxypropyl, γ-methoxybutyl, γ,ε-dimethoxyhexyl, β-n-propoxyethyl, β-ethoxyethyl, β-i-propoxyethyl, β-aminoethyl, β-aminopropyl, γ-aminopropyl, β-amino-γ-methylbutyl, N-methyl-β-aminoethyl, N-methyl-β-aminopropyl, N-methyl-γ-aminopropyl, N-methyl-β-amino-γ-methylbutyl, N,N-dimethyl-β-aminoethyl, N,N-dimethyl-β-aminopropyl, N,N-dimethyl-γ-aminopropyl, N,N-dimethyl-β-amino-γ-methylbutyl, N-ethyl-β-aminoethyl, N-ethyl-β-aminopropyl, N-ethyl-γ-aminopropyl, N-ethyl-β-amino-γ-methylbutyl, N,N-diethyl-δ-aminoethyl, N,N-diethyl-β-aminopropyl, N,N-diethyl-γ-aminopropyl, N,N-diethyl-β-amino-γ-methylbutyl, N-propyl-β-aminoethyl, N-propyl-β-aminopropyl, N-propyl-γ-aminopropyl, N-propyl-β-amino-γ-methylbutyl, N,N-dipropyl-β-aminoethyl, N,N-dipropyl-β-aminopropyl, N,N-dipropyl-γ-aminopropyl, N,N-dipropyl-β-amino-γ-methylbutyl, β-hydroxy-ε-aminopentyl, β-hydroxy-δ-aminobutyl, β-methoxy-δ-aminopentyl, β-ethoxy-δ-aminobutyl, β-methoxy-δ-N-methylaminobutyl, β-bromoisopropyl and β-chloroethyl.

The alkenyl and alkinyl radicals preferably have from 2 to 6 carbon atoms. Examples which may be mentioned are: allyl, crotyl, methallyl, β-methyl-β-butenyl, propin-2-yl and butin-2-yl. If they are substituted, they preferably carry one of the substituents listed above for alkyl.

Cycloalkyl and cycloalkenyl designate a cyclic radical having preferably from 3 to 10, in particular from 3 to 6, ring carbon atoms, which can contain from 1 to 3, in particular 1 or 2, identical or different substituents of the type mentioned for alkyl in the preceding text. Cycloalkylalkyl and cycloalkenylalkyl preferably represent cyclo-alk(en)ylmethyl or cycloalk(en)ylethyl, the cycloalk(en)yl radical being defined as indicated above. Examples of suitable cycloalk(en)yl and cycloalk(en)ylalkyl radicals are: cyclopropyl, cyclobutyl, cyclopentyl, cyclohexyl, cyclopropylmethyl, cyclopentylmethyl, cyclohexylmethyl, cyclohexylethyl and cyclohexenylmethyl. Aryl preferably designates a phenyl or naphthyl radical. The aryl radical can carry from 1 to 3 identical or different substituents, such as, for example, alkyl having preferably from 1 to 4 carbon atoms, halogen, preferably fluorine, chlorine or bromine, nitro, amino, monoalkylamino and dialkylamino having from 1 to 4 carbon atoms per alkyl group in each case, hydroxyl and alkoxythio and alkylthio having from 1 to 4 carbon atoms per alkyl group. Examples of aryl radicals are: o-ethylphenyl, m-ethylphenyl, p-ethylphenyl, p-hydroxyphenyl, nitrophenyl, aminophenyl and nitrobenzyl.

The aralkyl radicals are preferably phenylmethyl or phenylethyl radicals, which can carry any of the substituents mentioned above for aryl. Examples which may be mentioned are: β-phenylethyl and β-tolylethyl.

The aminoglycoside antibiotics of the formula (I) according to the invention which can be considered as being derived from the antibiotics gentamycin A, gentamycin B, gentamycin B$_1$, gentamycin C$_1$, gentamycin C$_{1a}$, gentamycin C$_2$, gentamycin C$_{2a}$, gentamycin C$_{2b}$, gentamycin X$_2$, sisomycin, JI-20A, JI-20B, verdamycin G52, G418, 66-40B, 66-40D, mutamycin 1, mutamycin 2, mutamycin 4, mutamycin 5 and mutamycin 6 in that the 3''-methylamino group present in the last mentioned antibiotics is replaced by a substituted amino group of the —NH—R type, R having the meaning indicated above, are of particular interest.

Of these, the sisomycin derivatives represented by formula (II)

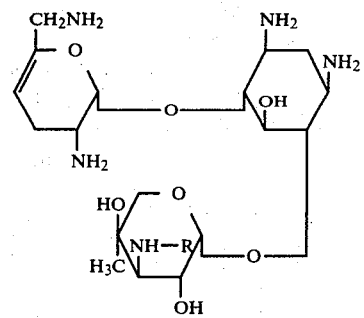

in which

R has the same meaning as defined hereinbefore in formula I are particularly valuable.

Examples of antibiotics of the formula (II) according to the invention are: 3''-N-demethyl-3''-N-ethylsisomycin, 3''-N-demethyl-3''-N-propylsisomycin, 3''-N-demethyl-3''-N-butylsisomycin, 3''-N-demethyl-3''-N-pentylsisomycin, 3''-N-demethyl-3''-N-isopropylsisomycin, 3''-N-demethyl-3''-N-heptylsisomycin, 3''-N-demethyl-3''-N-(β-dimethylpropyl)-sisomycin, 3''-N-demethyl-3''-N-allylsisomycin, 3''-N-demethyl-3''-N-(β-butenyl)-sisomycin, 3''-N-demethyl-3''-N-tolylethylsisomycin, 3''-N-demethyl-3''-N-(β-aminoethyl)-sisomycin, 3''-N-demethyl-3''-N-(β-methoxyethyl)-sisomycin, 3''-N-demethyl-3''-N-(γ-methoxybutyl)-sisomycin, 3''-N-demethyl-3''-N-(γ,ε-dimethoxyhexyl)-sisomycin, 3''-N-demethyl-3''-N-(β-butoxyethyl)-sisomycin, 3''-N-demethyl-3''-N-(β-propoxy-ethyl)-sisomycin, 3''-N-demethyl-3''-N-(β-ethoxyethyl)-sisomycin, 3''-N-demethyl-3''-N-(β-i-propoxyethyl)-sisomycin, 3''-N-demethyl-3''-N-(β-bromo-i-propyl)-sisomycin, 3''-N-demethyl-3''-N-(N'-methyl-β-aminoethyl)-sisomycin, 3''-N-demethyl-3''-N-(N',N'-di-methyl-β-aminoethyl)-sisomycin and 3''-N-demethyl-3''-N-(N',N'-diethyl-β-aminoethyl)-sisomycin.

The invention also includes the acid addition salts, especially the pharmaceutically usable acid addition salts, of the new aminoglycoside antibiotics.

Salts of the above-mentioned acids or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

The invention furthermore provides a process for the production of a compound of the invention, in which a compound of the formula (III)

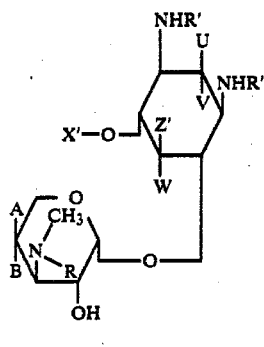 (III)

in which
A is hydroxyl or hydrogen,
B is hydroxyl, hydrogen or methyl,
R, U, V and W have the same meaning as defined hereinbefore in formula I,
Z' is hydrogen, hydroxyl or amino or amino which is protected by an amino-protective group (R') such as is defined below,
and in which
X' represents a radical of the formula

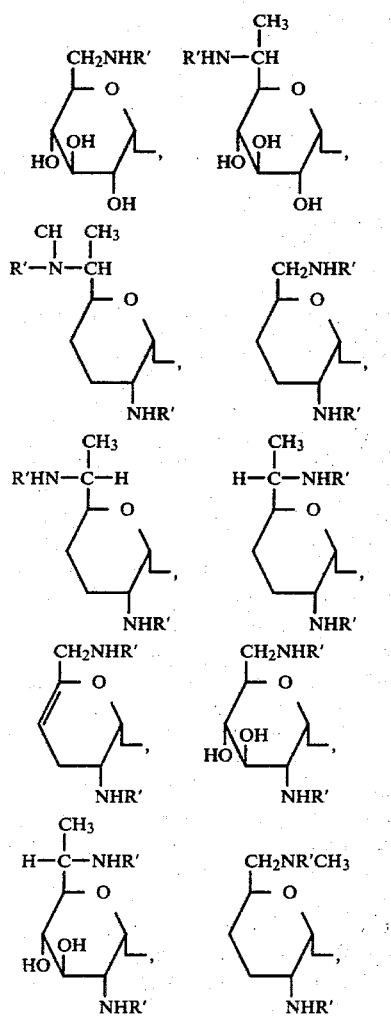

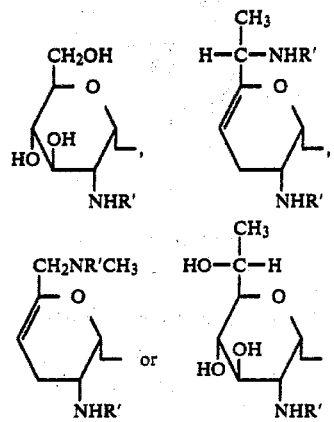

wherein R' is an amino-protective group, is treated with an oxidising agent, generally at a temperature of from −20° C. to 100° C., preferably in the presence of a diluent which is inert under the reaction conditions, the 3''-N-methyl group bein split off but the radical R (which is other than methyl) remaining unattacked;

removing any amino-protective group(s) which may be present, and where the pseudotrisaccharide of the formula (I) is obtained in the free form or, in the form of an acid addition salt thereof, optionally converting it into a salt thereof or the corresponding free pseudotrisaccharide, respectively.

All the protective groups which are stable under the oxidation conditions of the process described above and are customary in the field of amino-sugar chemistry and peptide chemistry can be used as the amino-protective groups R'. Such protective groups and the processes for introducing them are known (see, for example, Houben-Weyl, Methoden der organischen Chemie (Methods of organic Chemistry), volume XV, 1, Georg Thieme Verlag, Stuttgart, 1974).

Preferred examples of such protective groups are acyl groups of the formula (1) or (2)

 (1)

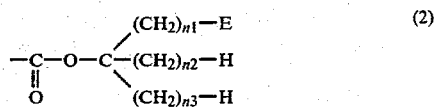 (2)

wherein
D and E are the same or different and each is hydrogen, phenyl or substituted phenyl and
n, $n_1$, $n_2$ and $n_3$ are the same or different and each represents a number from 0 to 5.

The starting materials used according to the invention are aminotrisaccharides, which are in themselves known from the literature, of the general formula (IV)

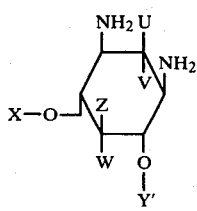
(IV)

wherein
X has the same meaning as defined hereinbefore in formula (I) and
Y' designates a radical of the formula

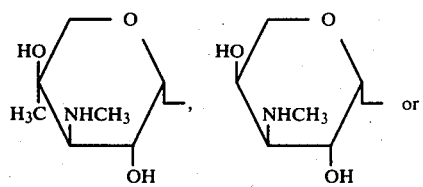 or 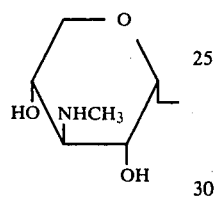

Examples of such trisaccharides are sisomycin, gentamycins, mutamycins and the antibiotics 66-40 B and 66-40 D. For the preparation of the selectively N-blocked aminotrisaccharides of the formula (III) (wherein R' in each case designates an amino-protective group) used as starting materials according to the invention, an aminotrisaccharide of the formula (IV) may be reacted, with a compound of the formula (V)

G'—F      (V)

in which
F represents, for example, a radical of the formula (1) or (2) as defined hereinbefore and
G' is halogen or a leaving group which is customary in acylation reactions, preferably an activated ester group, or a group

F—O— in which
F has the same meaning as defined hereinbefore in formula (V), generally in an inert organic solvent, optionally with the addition of water, usually at a temperature of from −80° C. to +50° C., if appropriate in the presence of a base, and the reaction product is worked up in the customary manner. The meaning of the expression "leaving group" is defined in Houben-Weyl, Methoden der organischen Chemie, Band XV, 2, Seiten 1-364, Georg Thieme Verlag, Stuttgart, 1974).

Pseudotrisaccharides in which all the amino groups, with the exception of the 3″-N-methylamino group, are blocked by protective groups are obtained in this manner. Preferably the same perotective group R' is used for protecting each amino group in the molecule.

If, for example, sisomycin is used as the starting substance and pyrocarbonic acid diethyl ester is used as the acylating agent, reaction is aqueous ethanol gives quantitatively, 1,2′,3,6′-tetra-N-ethoxycarbonyl-sisomycin of the formula (VI)

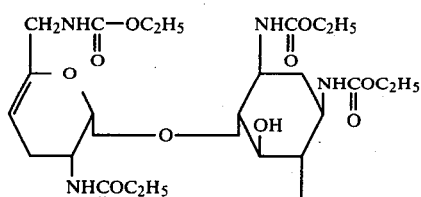

The selectively N-blocked pseudotrisaccharides which are generally obtainable in this manner can be represented by the general formula (VII)

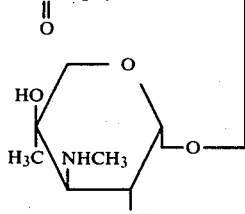

wherein
X', R', U, V, W, Z', A and B have the same meaning as defined hereinbefore in formula (III).

The invention also includes processes, according to which the selectively protected pseudotrisaccharides of the formula (VII) are N-alkylated on the 3″-methylamino group, 3″-N-alkyl derivatives of the formula (III), in which the newly introduced radical R has the meaning indicated above, being obtained.

One of the preferred processes, according to the invention, for the preparation of the 3″-N-substituted derivatives of the 4,6-di-O-(aminoglycosyl)-1,3-diaminocyclitols of the formula (III), which contain amino-protective groups in all the positions with the exception of the 3″-position, comprises reacting a compound according to the formula (VII), or acid addition salt thereof, with an aldehyde of the formula R″-CHO, wherein R″CH$_2$ has the same meaning as defined hereinbefore for R and, in the case where this radical contains an amino group and/or hydroxyl group, can also contain an amino-protective group and/or hydroxyl-protective group, in the presence of a hydrogen donor reducing agent, and working up the mixture in a manner which is in itself known so as to produce a compound of the formula (III), and optionally splitting off the protective group(s) present. Such protective groups and the processes for introducing them are known (see, for example, Methods in Carbohydrate Chemistry Volume I, pp. 150–400, Academic Press, New York, 1963).

This process, in which the 3″-amino group in a 4,6-di-O-(aminoglycosyl)-1,3-diaminocyclitol is reacted with an aldehyde and simultaneously reduced in situ is usually carried out at room temperature in the presence of air, although it can be more advantageous to carry out the reaction under an inert gas (argon or nitrogen). The reaction is usually very rapidly completed, frequently in less than 60 minutes, which can be established by thin layer chromatography examination of the reaction mixture.

Hydrogen donor reducing agents which may be used in this process include dialkylaminoboranes (for example dimethylaminoborane, diethylaminoborane and, preferably, morpholinoborane), tetraalkylammonium cyanoborohydrides (for example tetrabutylammonium cyanoborohydride), alkali metal borohydrides (for example sodium borohydride) and, preferably, alkali metal cyanoborohydrides (for example lithium cyanoborohydride and sodium cyanoborohydride).

The process is usually carried out in an inert solvent. The solvent can be an organic or inorganic solvent in which the selectively protected 4,6-di-O-(aminoglycosyl)-1,3-diaminocyclitol and the other reagents are soluble and which as far as possible decreases or prevents side reactions under the reaction conditions. Although anhydrous aprotic solvents can be advantageously employed (for example tetrahydrofurane if the reducing agent is morpholinoborane), a protic solvent is customarily used. Examples of suitable protic solvents are a lower alkanol, such as methanol, ethanol, n-propanol, i-propanol etc. or, preferably, water or an aqueous lower alkanol, preferably aqueous methanol or ethanol, n-propanol or i-propanol or other solvent systems which contain water, such as, for example, aqueous dimethylformamide aqueous hexamethylphosphoramide, aqueous tetrahydrofurane or aqueous ethylene glycol dimethyl ether. protic solvents are a lower alkanol or, preferably, water or an aqueous lower alkanol, preferably aqueous methanol or ethanol, or other solvent systems which contain water, such as, for example, aqueous dimethylformamide, aqueous hexamethylphosphoramide, aqueous tetrahydrofurane or aqueous ethylene glycol dimethyl ether.

The process is usually carried out at a pH in the range from 1 to 11, and preferably at a pH of from 4 to 8.

Typical aldehydes of the formula R″CHO, in which R″ is as defined above, which can be used in the process include straight-chain or branched alkylaldehydes, such as acetaldehyde, n-propanal, n-butanal, 2-methylpropanal, n-pentanal, 2-methylbutanal, 3-methylbutanal, 2,2-dimethylpropanal, n-hexanal, 2-ethylbutanal, n-heptanal and n-octanal; alkenylaldehydes, such as propenal, 2-methylpropenal, 2-butenal, 2-methyl-2-butenal and 2-ethyl-2-hexenal; cyclic aldehydes, such as cyclopropanecarbaldehyde, cyclopentanecarbaldehyde, cyclopentaneacetaldehyde and cyclohexanecarbaldehyde; benzaldehyde, o-, m- and p-toluenecarbaldehyde and phenylacetaldehyde; straight-chain and branched alkylaldehydes substituted by hydroxyl, such as 5-hydroxypentanal, 2-hydroxy-3-methylbutanal, 2-hydroxy-2-methylpropanal, 4-hydroxybutanal, 2-hydroxypropanal and 8-hydroxyoctanal as well as glyceraldehyde; straight-chain and branched alkylaldehydes substituted by amino, such as 5-aminopentanal, 2-aminopropanal, 3-aminopropanal, 4-aminobutanal, 2-amino-3-methylbutanal and 8-amino-octanal and mono-N-alkyl derivatives thereof; and straight-chain and branched akylaldehydes disubstituted by amino and hydroxyl, such as 2-hydroxy-5-aminopentanal, 3-hydroxy-3-methyl-4-aminobutanal, 2-hydroxy-4-aminobutanal, 2-hydroxy-3-aminopropanal, 2-hydroxy-2-methyl-3-aminopropanal and 2-amino-3-hydroxyoctanal and mono-N-alkyl derivatives thereof.

If an aldehyde with an optically active centre is used in this process, it is possible to use each enantiomer separately or the racemate and the corresponding diastereoisomers or a mixture thereof are obtained respectively.

The aldehydes used in the process are either known compounds or can be easily prepared from known compounds by conventional processes.

In carrying out the process, it may be advantageous to protect the amino group of an aldehyde which contains an amino group, for example, by forming an acetamido or phthalimide or ethoxycarbonyl derivative thereof, and to liberate the amino group after the reaction has been completed. It can also be advantageous to protect any hydroxyl groups in the aldehydes, but in general this is not necessary.

It is also possible to use an acetal or hemiacetal of the aldehyde if the reaction is carried out in an acid medium, which gives rise to the in situ formation of the free aldehyde.

The process is preferably carried out by adding from 1 to 10 equivalents of the particular aldehyde (for example acetaldehyde) to a solution of the 4,6-di-O-(aminoglycosyl)-1,3-di-aminocyclitol, which contains amino-protective groups in all the positions with the exception of the 3″-position (for example 1,2′,3,6′-tetra-N-ethoxycarbonylsisomycin) in aqueous methanol, and thereafter (after about 0.5 hour) adding approximately 1.3 equivalents of an alkali metal cyanoboranate (for example sodium cyanoboranate). Working up by customary methods gives the desired 3″-NR derivative of the corresponding protected pseudotrisaccharide (for example 3″-N-ethyl-1,2′,3,6′-tetra-N-ethoxycarbonylsisomycin).

Another process, according to the invention, for the preparation of the 3″-N-alkylated derivatives of the 4,6-di-O-(aminoglycosyl)-1,3-diaminocyclitols of the formula (III) comprises reacting a compound of the formula (VII) with a halogen compound of the formula (3)

R—Hal (3)

wherein
R has the same meaning as defined hereinbefore in formula I, and
Hal denotes halogen, such as chlorine, bromine or iodine.

Such alkylations of amines are already known from the literature (see, for example, Houben-Weyl, Methoden der organischen Chemie (Methods of organic Chemistry), volume XI, 1, Georg Thieme Verlag, Stuttgart, 1957). These alkylations are preferably carried out in the presence of a diluent which is inert under the reaction conditions, preferably a diluent in which the reactants readily dissolve. Preferred diluents of this type are ethers, such as tetrahydrofurane, ethyl ether ethylene glycol dimethyl ether or dioxane ketones, such as acetone or methyl ethyl ketone, alcohols, dimethylacetamide and dimethylformamide. The use of dimethylformamide as the solvent is particularly preferred here. Depending on the reactivity of the alkyl halide employed, from 1 to 10 molar equivalents of alkylating agent are preferably used and the reaction is generally carried out at a pH value of from 5 to 12. The use of an auxiliary base for trapping the hydrogen halide liberated during the reaction is to be preferred here. Examples of appropriate bases are alkali metal hydroxides, alkaline earth metal hydroxides, alkali metal carbonates and alkaline earth metal carbonates, alkaline earth metal oxides and carbonates and oxides of heavy metals, such as, for example, lead carbonate and silver carbonate as well as mercury oxide or silver oxide. In principle, all the compounds which are stable under the reaction conditions and are capable of trapping the hydrogen halide formed can be used as auxiliary bases.

The reaction according to the invention is generally carried out at a temperature of from $-20°$ C. to $+80°$ C., preferably from $0°$ to $30°$. The reaction time is usually from 1 to 48 hours and in general the reaction is carried out under normal pressure. After customary working-up, the desired 3"-N-substituted derivatives are obtained in the pure form and usually in quantitative yield.

Further processes for alkylating compounds of the formula (VII) in order to prepare compounds of the formula (III) comprise reacting said compounds of formula (VII) with sulphuric acid esters and sulphonic acid esters, epoxides and compounds with activated double bonds and are familiar to the skilled person.

The invention furthermore includes processes for selectively splitting off the methyl group from the 3"-N(CH$_3$)$_R$-trisaccharides of the formula (III) obtained with the aid of the alkylation methods described above.

One of the preferred processes, according to the invention, for splitting off the methyl group is the oxidative demethylation of the tertiary 3"-amino group.

The customary oxidising agents can be used for splitting (demethylating) the compounds according to formula (III).

Examples of oxidising agents are heavy metal salts, peroxides, halogens, halogen oxyacids and their salts, nitrogen oxides and molecular oxygen. Preferred oxidising agents are permanganates, manganates, manganese dioxide, chromium trioxide, bichromates, chromates, alkyl chromates, chromyl chloride, selenium dioxide, cobalt-III salts, Cer-IV salts, potassium hexacyanoferrate-III, copper oxide, lead oxide, mercury oxide, mixtures of hydrogen peroxide with iron-II salts, iron-III salts, selenium dioxide, osmium tetroxide, vanadates, tungstic acid and/or chromic acid, lead tetraacetate, chlorine, bromine, iodine, hypochlorates, chlorites, hypobromates, bromates, periodates, dinitrogen monoxide, nitrogen dioxide and air. If molecular oxygen is used, noble metals, such as platinum, palladium, rhodium, ruthenium or rhenium, as well as nickel, are preferably used as catalysts.

Particularly preferred oxidising agents are manganese dioxide, potassium hexacyanoferrate-III and potassium permanganate. In the case that potassium hexacyanoferrate-III is the oxidising agent and ammonium hydroxide is the base, copper-(II) sulfate can be added to the solution which should be oxidised. Under these conditions hexacyanoferrate-II precipitates as the difficultly soluble copper salt.

The splitting reaction is preferably carried out in the presence of a diluent which is inert under the reaction conditions, preferably a diluent in which the reactants dissolve. Suitable diluents of the type mentioned are water or mixtures of water with methanol, ethanol, i-propanol, tetrahydrofurane, dimethylformamide, dioxane, pyridine, ethylene glycol dimethyl ether and acetone.

Depending on the nature of the oxidising agent used, the reaction according to the invention is generally carried out at a pH value of from 3 to 12. Adjustment of the pH value can be achieved by adding an appropriate acid or base. Those acids or bases which do not decompose the starting compounds or the end products and do not cause a decrease in the activity of the oxidising agents can be used here. Rather, it is desirable for them to increase the activity of the oxidising agents. Examples of inorganic acids which can be used are hydrochloric acid and sulphuric acid and examples of organic acids which can be used are acetic acid and formic acid. Examples of appropriate bases are ammonium hydroxide, alkali metal hydroxides, alkaline earth metal hydroxides, alkali metal carbonates, alkaline earth metal carbonates, alkali metal alcoholates and alkali metal salts and alkaline earth metal salts of carboxylic acids.

The pH value can be adjusted either before the start of the reaction or during the reaction.

The reaction according to the invention is carried out at a temperature of from $-20°$ to $100°$ C., preferably from $-5°$ to $70°$ C. The reaction time is half an hour to 50 hours. In general, the reaction is carried out under normal pressure.

The protective groups present in the molecule after the reaction is split off in a known manner by alkaline or acid hydrolysis, hydrogenolysis or displacement reactions. If compounds which contain acyl protective groups of the formula (1) or (2) are employed for the splitting reaction, these groups can preferably be split off using aqueous solutions of alkali metal hydroxides or alkaline earth metal hydroxides.

The processes, according to the invention, described above are illustrated by the following equation using the preparation of 3"-N-ethyl-3"-N-demethylsisomycin of the formula (II), in which R=C$_2$H$_5$, starting from sisomycin as an example.

$$\text{Sisomycin} \xrightarrow[\text{CH}_3\text{OH/H}_2\text{O}]{\text{acetanhydride}} \text{VIII}$$

(II, R = CH$_3$)

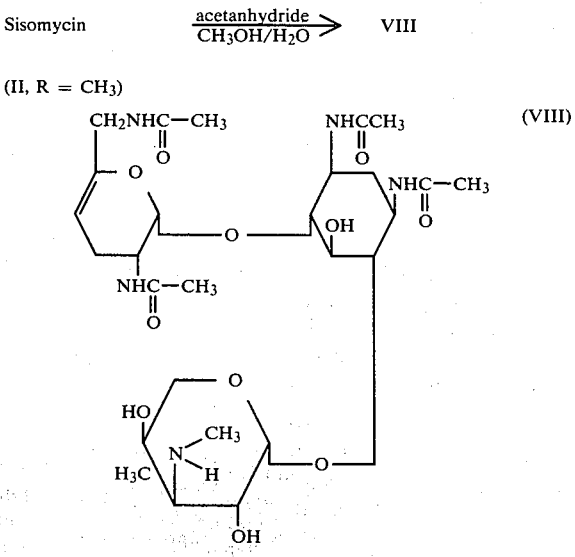

(VIII)

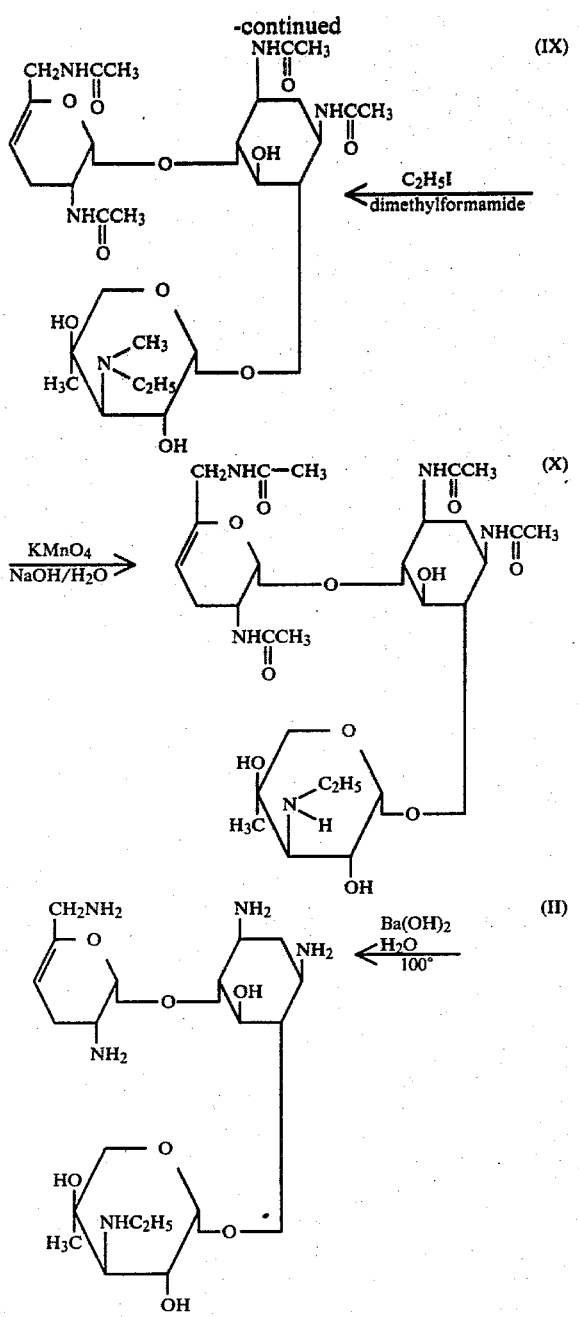

The 1,2',3,6'-tetra-N-acetylsisomycin (VIII) used according to the invention is accessible, in quantitative yield by reacting sisomycin with acetic anhydride in methanol/water.

The ethyl group is subsequently introduced in the 3''-nitrogen by reacting (VIII) with ethyl iodide in dimethylformamide as the solvent and with, for example, silver oxide as the base. The mixture is worked up in a manner which is in itself known and 3''-N-ethyl-1,2',3,6'-tetra-N-acetylsisomycin (IX) is obtained in quantitative yield. In order to split off the 3''-N-methyl group, (IX) is treated with potassium permanganate in aqueous acetone, sodium hydroxide being added as the base. After completion of the reaction, which is determined by thin layer chromatography, the inorganic salts are precipitated by adding acetone and the 3''-N-demethyl compound (X) is isolated in high yield from the solution which remains. The acetyl protective groups are split off by heating the compound in aqueous barium hydroxide solution, and the hitherto unknown 3''-N-ethyl-3''-N-demethylsisomycin is thus obtained.

The 3''-N-methyl group can also be split off from the 3''-N derivatives of the formula (III) by reaction with cyanogen bromide. The cyanamides thereby formed can be easily converted into the corresponding secondary amines of formula (XI) (in which R'''=H), for examples by heating with dilute acids. The splitting off of the 3''-N-methyl group can be accomplished in that the 3''-N-derivatives of formula III are oxidised according to conventional methods with $H_2O_2$ at the tertiary 3''-amino group to the corresponding N-oxide which is converted by means of acetic acid anhydride to the 3''-N-Acetyl-3''-N-alkyl-3''-N-desmethyl-1,2',-3,6'-tetra-N-acyl compound. After splitting off of the acetyl group the 3''-N-alkyl-3''-desmethyl derivatives with free amino groups are obtained.

The reaction with chloroformic acid esters, phosgene and carboxylic acid halides, such as benzoyl chloride, with 3''-N—($CH_3$)R derivatives of pseudotrisaccharides of the formula (III) proceeds similarly to the action of cyanogen bromide, the 3''-methyl radical being split off and the corresponding 3''-N-acyl derivatives of the formula (XI) (in which R'''=acyl), which can be saponified to give the corresponding free amines of the formula (I), being formed.

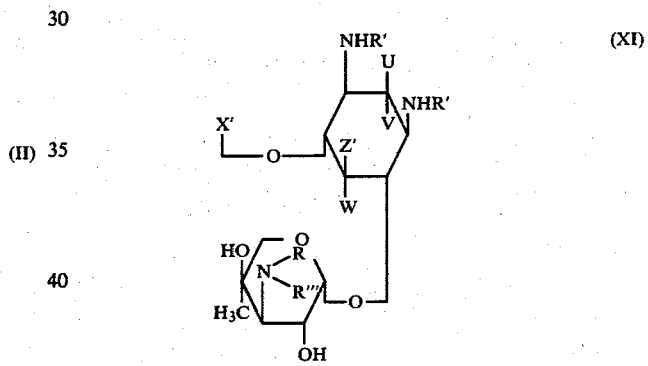

The symbols X', R', U, V, Z', W, A, B and R here have the same meaning as defined hereinbefore in formula I and elsewhere. R''' can be hydrogen or acyl.

The corresponding unprotected compounds of the formula (XII)

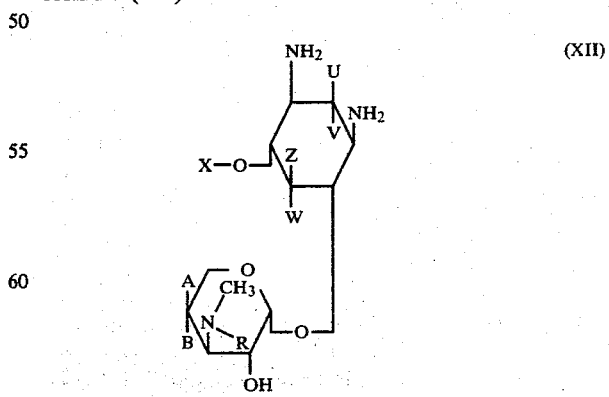

wherein
the amino groups present in the molecule are in the free form, can also be employed for the oxidative demethylation. In (XII), A, B, U, V, W, X, Z and R have the same meaning as defined hereinbefore in formula I and elsewhere.

The compounds according to the invention are antibacterial agents with a broad spectrum of action and a particular activity against Gram-negative bacteria. These properties make it possible for them to be used as medicaments in combating bacterial diseases in warm-blooded animals. They are suitable for the prophylaxis and chemotherapy, in medicine, of local and systemic infections, especially infection of the urogenital system, which are caused by Gram-negative bacteria, for example *E. coli,* Proteus, Klebsiella and Pseudomonas. Inhibition depths in the agar hole test were found, for example, against the following bacteria strains at a concentration of 100 micrograms/1 ml; *Pseudomonas aerug.* 5737, *Pseudomonas aerug.* F 41, *Klebsiella pneum.* 2 Munich, *Klebsiella pneum.* 1 Düsseldorf, *E. coli* Münster and *E. coli* Neumann.

As stated above, the invention also relates to the use in medicine of the compounds of the invention.

The present invention provides a pharmaceutical composition containing as active ingredient a compound of the invention in admixture with a solid or liquefied gaseous diluent, or in admixture with a liquid diluent other than a solvent of molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this specification means physically discrete coherent portions suitable for medical administration. "Medicament in dosage unit form" as used in this specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third, or a quarter of a daily dose will depend on whether the medicament is to be administered once or, for example, twice, three times or four times a day, respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate, (h) adsorptive carriers, e.g. kaolin and bentonite; (i) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above mentioned diluents.

The diluents to be used in pharmaceutical compositions adapted to be formed into suppositories can, for example, be the usual water-soluble or water-insoluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5, usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted, by virtue of their shape or packaging, for medical administration and may be, for example, any of the following: tablets, (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is from 20 to 2000, most preferably from 100 to 500 mg of active ingredient.

The production of the above mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously or intravenously), rectally or topically, preferably orally, parenterally or topically. Preferred pharmaceutical compositions and medicaments are therefore those adapted for oral, parenteral or topical administration, such as tablets, capsules or elixirs, injection solutions or suspensions, or ointments, creams, or lotions, respectively. Administration in the method of the invention is preferably orally, parenterally or topically.

In general it has proved advantageous to administer amounts of from 0.4 to 40, preferably from 2 to 10 mg/kg of body weight per day to achieve effective results. Nevertheless, it can at times be necessary to deviate from those dosage rates, and in particular to do so as a function of the nature and body weight of the subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above mentioned minimum dosage rate, whilst other cases the upper limit mentioned must be exceeded to achieve the desired results. Where larger amounts are administered it can be advisable to divide these into several individual administrations over the course of the day. Thus, for example; injection solutions or suspensions are usually administered at a rate of 1 to 15 mg of active compound per kg of body-weight in from 2 to 4 doses per day. Topical formulations containing, for example, from 0.1 to 3.0 g. of the compound of the invention per 100 g of ointment cream or lotion are conveniently applied from 2 to 5 times daily.

| Tablet | Formulation 1 | | |
|---|---|---|---|
| | 10 mg tablet | 25 mg tablet | 10 mg tablet |
| 3''-N-Dimethyl-2''-N-ethyl-sisomycin | 10.50+ mg | 26.25+ mg | 105.00+ mg |
| Lactose | 197.50 mg | 171.25 mg | 126.00 mg |
| Maize starch | 25.00 mg | 25.00 mg | 35.00 mg |
| Polyvinyl-pyrrolidone | 7.50 mg | 7.50 mg | 7.50 mg |
| Magnesium stearate | 2.50 mg | 2.50 mg | 3.50 mg |

+5% excess

Preparation

A suspension of 3''-N-demethyl-ethylsisomycin, lactose and polyvinylpyrrolidone is prepared and this is spray-dried. The maize starch and the magnesium stearate are added and the omponents are mixed and pressed to tablets.

| Formulation 2 | |
|---|---|
| Ointment | |
| 3''-N-Demethyl-3''-N-ethylsisomycin | 1.0 g |
| Methylparaben U.S.P. | 0.5 g |
| Propylparaben U.S.P. | 0.1 g |
| Petrolatum | to 1,000 g |

Preparation (1) The petrolatum is melted;
(2) 3''-N-Demethyl-3''-N-ethylsisomycin, Methylparaben and Propylparaben are mixed with about 10% of the molten petrolatum;
(3) The mixture is put into a colloid mill; and
(4) The remaining petrolatum is added, whilst stirring, and the mixture is cooled until it becomes semi-solid. The product is filled into suitable containers.

| Injection solution | Formulation 3 | |
|---|---|---|
| | per 2.0 ml phial | per 50 liters |
| 3''-N-Demethyl-3''-N-ethylsisomycin | 84.0 mg+ | 2,100.0 gm |
| Methylparaben, U.S.P. | 3.6 mg | 90.0 gm |
| Propylparaben, U.S.P. | 0.4 mg | 10.0 gm |
| Sodium bisulphite, U.S.P. | 6.4 mg | 160.0 gm |
| Disodium ethylenediamine-tetraacetate dihydrate | 0.2 mg | 5.0 gm |
| Water, U.S.P. q.s. | 2.0 mg | 50.0 liters |

+5% excess

EXAMPLE 1

1,2',3,6'-Tetra-N-(ethoxycarbonyl)-sisomycin 1.1 g of sisomycin are dissolved in 50 ml of ethanol and 70 ml of water. After cooling the solution to $-10°$ C., 1.35 ml of pyrocarbonic acid diethyl ester are added dropwise, whilst stirring well. After a further 2½ hours at $-10°$ C., 100 ml of water are added. The mixture is then extracted with 150 ml of petroleum ether and the aqueous phase is evaporated to dryness in vacuo. The residue is dissolved in methanol. The desired product is precipitated by adding excess ether and petroleum ether.

Yield=1.5 g (91%)

$^{13}$C-NMR(CD$_3$OD/CDCl$_3$): δ=50.86 (C-1); 49.90 (C-2); 46.33 (C-2'); 42.87 (C-6'); 157.94, 157.73, 157.29 and 157.22 (>c=o) ppm.

EXAMPLE 2

1,2',3,6'-Tetra-N-acetyl-sisomycin 1.1 g of sisomycin are dissolved in 120 ml of water. After adding 60 ml of methanol, 2.5 ml of acetic anhydride are added dropwise to the mixture, whilst stirring. After 15 minutes, the mixture is evaporated to dryness in vacuo. The residue is dissolved in 10 ml of methanol and this solution is added dropwise to a mixture of 30 ml of ether and 30 ml of petroleum ether, whereupon the desired product precipitates.

Yield=1.43 g, mass spectrum: m/e=615.

$^{13}$C-NMR (CD$_3$OD): δ=50.14 (C-1); 49.20 (D-3); 46.88 (C-2'); 42.26 (C-6'); and 173.24, 173.13 and 173.63 (>c=o) ppm.

EXAMPLE 3

3''-N-Ethyl-1,2',3,6-Tetra-N-acetyl-sisomycin 1.9 g of the tetra-N-acetylsisomycin prepared according to Example 2 are dissolved in 30 ml of dimethylformamide and 2 g of silver oxide and then 0.6 ml of ethyl iodide in 3 ml of dimethylformamide are added at 0° C., whilst stirring. After stirring the mixture overnight, 10 ml of methanol and 25 ml of methylene chloride are added, the mixture is decolorised with wood charcoal and filtered and the filtrate is evaporated in vacuo. The desired product is thus obtained as a colourless solid. Yield 1.9 g. $(α)_D^{22}$ = +168°(c=1.0, CH$_3$OH)

EXAMPLE 4

3''-N-p-Nitrobenzyl-1,2',3,6'-tetra-N-acetyl-sisomycin 1.3 g of the product from Example 2 in 20 ml of dimethylformamide are stirred with 2.5 g of silver oxide and 2.2 g of p-nitrobenzyl bromide at room temperature for 1 hour. The mixture is then diluted with 50 ml of chloroform, stirred briefly with a little wood charcoal and filtered. The filtrate is evaporated to dryness in vacuo and the residue is reprecipitated from chloroform with petroleum ether. Yield=1.1 g $^{13}$C-NMR (CD$_3$OD): δ=62.02 (CH$_2$—Ar); 124.39, 131.00 and 148.57 (aromatic H); 102.05 (C-1''); and 67.03 (C-3'') ppm.

EXAMPLE 5

3''-N-Cyclohex-3-enylmethyl-1,2'-3,6'-tetra-N-acetyl-sisomycin 650 mg of the product from Example 2 in 3 ml of water are stirred with 150 mg of 1,2,5,6-tetrahydrobenzaldehyde in 10 ml of methanol at room temperature for 30 minutes. After adding 95 mg of sodium cyanoborate, the mixture is stirred at room temperature for a further 10 hours. For working up, the reaction mixture is filtered over a short column containing a basic ion exchanger OH$^θ$ form, Lewatit ® MP 500, Bayer, Leverkusen), the filtrate is evaporated to dryness in vacuo, the residue is extracted with methylene chloride/methanol in the ratio 1/1, the undissolved material is filtered off and the filtrate is evaporated to dryness in vacuo. Yield: 600 mg of a colourless solid (diastereomer mixture).

$^{13}$C-NMR (CD$_3$OD/CDCl$_3$): δ=33.60, 33.35, 27.95, 27.48, 25.74 and 25.45 (ring methylenes); 127.55; 126.95 (>c=c<); and 67.46 (C-3'') ppm.

EXAMPLE 6

3''-N-(β-Methylallyl)-1,2',3,6'-tetra-N-acetyl-sisomycin 130 mg of the product from Example 2 are dissolved in 2 ml of dimethylformamide, and 90 mg of 3-chloro-2-methylprop-L-ene and 200 mg of silver oxide are added at 0° C. The mixture is stirred at room temperature for a further 24 hours, 2 ml of methanol and 2 ml of methylene chloride are added, and the mixture is worked up as described in Example 3. Colourless solid, melting point=158° C. RF value 0.68 (Running agent system B=chloroform:methanol:15% strength NH$_3$/H$_2$O in the ratio 1:1:1; thin layer chromatography finished plates, silica gel 60-F254 from Messrs. E. Merck, Darmstadt).

EXAMPLE 7

3''-N-(β,γ-Dihydroxypropyl)-1,2',3,6'-tetra-N-acetyl-sisomycin 400 mg of glyceraldehyde in 30 ml of methanol are added to 2.6 g of 1,2',3,6'-tetra-N-acetyl-sisomycin in 30 ml of water and the mixture is stirred at room temperature for 45 minutes. 360 mg of sodium cyanoboranate are then added and the mixture is heated under reflux for 7.5 hours. It is worked up as described in Example 5. 2.5 g of a colourless solid (diastereomer mixture) are obtained. Melting point=130°-140° (decomposition).

EXAMPLE 8

3''-N-Dimethyl-3''-N-ethyl-1,2',3,6'-tetra-N-acetyl-sisomycin 2 g of 3''-N-ethyl-1,2',3,6'-tetra-N-acetyl-sisomycin (see Example 3) are dissolved in 22 ml of water and 5 ml of acetone and, after adding 400 mg of potassium hydroxide in 5 ml of water, the solution is cooled to 0°. 500 g of potassium permanganate in 50 ml of water are then added dropwise, whilst stirring well and cooling. After 1.5 hours, the inorganic salts are precipitated by adding 70 ml of acetone. The undissolved material is filtered off, the filtrate is evaporated in vacuo and the residue thus obtained is extracted with methanol/chloroform. The extract is again filtered, the filtrate is evaporated in vacuo and the crude product thus obtained is purified by filtration through a silica gel column.

The title compound is obtained as an amorphous solid in this manner.

$^{13}$C-NMR (CD$_3$OD): δ=100.87 (C-1''); 70.39 (C-2''); 63.83 (C-3''); 51.17 (C-1); 34.65 (C-2); 50.09 (C-3); 97.63 (C-1'); 46.58 (C-2'); and 15.12 (CH$_2$-CH$_3$) ppm.

EXAMPLE 9

3''-N-Demethyl-3''-N-ethyl-sisomycin

In order to split off the acetyl groups, the product obtained according to Example 8 is dissolved in 30 ml of water and, after adding 20 g of barium hydroxide hydrate, the mixture is heated to the reflux for 5 hours. For working up, the dissolved barium salts are precipitated as barium carbonate. The mixture is filtered, the filtrate is evaporated to dryness in vacuo, the residue thus obtained is extracted with methanol/methylene chloride and the undissolved material is filtered off. Evaporation of the filtrate gives the title compound as a colourless solid.

$(\alpha)_D^{20} = +179°$ (c=1,0 H$_2$O) Rf=0.27 (Running agent system A=chloroform:methanol:20% strength NH$_3$/H$_2$O in the ratio 2:4:1).

EXAMPLE 10

3''-N-Demethyl-3''-N-propyl-sisomycin 400 mg of 1,2',3,6'-tetra-N-acetyl-sisomycin are dissolved in 5 ml of methanol and 1 ml of water. 200 mg of propionaldehyde are added to the solution and the mixture is left at room temperature for 0.5 hours. 100 mg of sodium cyanoboranate are now added and the mixture is allowed to react at room temperature for a further 3 hours. It is worked up as described in Example 5 and 400 mg of 3''-N-propyl-1,2',3,6'-tetra-N-acetyl-sisomycin are thus obtained and are fed, in the form of the crude product, to the oxidative desmethylation. For this, the product is dissolved in 4.5 ml of water and 1 ml of acetone, and 85 mg of potassium hydroxide in 1 ml of water are added to this solution. After cooling to 0°, 100 mg of potassium permanganate in 10. 5 ml of water are slowly added dropwise to the mixture, whilst stirring well. After 1.5 hours at room temperature, the mixture is diluted with 25 ml of acetone, the undissolved material is filtered off and the filtrates are evaporated to dryness in vacuo. The crude product thus obtained is chromatographed over a short column of silica gel for final purification (eluting agent: Running agent system A)

In order to split off the N-acetyl groups, the 3''-N-demethyl-3''-N-propyl-1,2',3,6'-tetra-N-acetyl-sisomycin thus obtained is dissolved in 6 ml of water, 4 g of barium hydroxide hydrate are added and the mixture is heated to the reflux for 5 hours. For working up, the dissolved barium salts are precipitated as barium carbonate. The mixture is filtered, the filtrate is evaporated to dryness in vacuo, the residue thus obtained is extracted with methanol/methylene chloride and the undissolved material is filtered off. Evaporation of the filtrate gives the title compound as a colourless solid. Rf value=0.32 (Running agent system A)

The following 3''-N-demethyl-3''-N-alkyl-sisomycins are prepared as described in Example 10:
1. 3''-N-Desmethyl-3''-N-n-butyl-sisomycin Rf=0.35
2. 3''-N-Desmethyl-3''-N-n-pentyl-sisomycin Rf=0.37
3. 3''-N-Desmethyl-3''-N-n-heptyl-sisomycin Rf=0.40
4. 3''-N-Desmethyl-3''-N-(β-dimethylpropyl)-sisomycin Rf=0.38
5. 3''-N-Desmethyl-3''-N-(β-methoxybutyl)-sisomycin Rf=0.48
6. 3''-Desmethyl-3''-N-(γ,β-dimethoxyhexyl)-sisomycin Rf=0.53

The running agent system for determining the Rf values is in each case chloroform: methanol: 20% strength NH$_3$/H$_2$O in the ratio 1:1:1 Rf of sisomycin=0.18

EXAMPLE 11

3''-N-Dimethyl-3''-N-β-aminoethyl-sisomycin

The reductive alkylation of 400 mg of 1,2',3,6'-tetra-N-acetyl-sisomycin in 8 ml of methanol and 1 ml of water using N-ethoxycarbonylaminoacetaldehyde gives 380 mg of 3''-N-(β-ethoxycarbonylaminoethyl)-1,2',3,6'-tetra-N-acetyl-sisomycin, which is desmethylated as described in Example 10 and then deacylated. The title compound is thus obtained as an amorphous solid. Rf=0.10 (Running agent system A).

EXAMPLE 12

3''-N-Dimethyl-3''-N-methoxyethyl-sisomycin 220 mg of methoxyacetaldehyde diethyl acetal are dissolved in 2 ml of H$_2$O and 4 ml of methanol. The pH is adjusted to 1 with dilute sulphuric acid and the mixture is heated to the reflux for 10 minutes and then neutralised with dilute sodium hydroxide solution. 400 mg of 1,2',3,6'-tetra-N-acetyl-sisomycin are added, the mixture is left at room temperature for 0.5 hour and 100 mg of sodium cyanoboranate are then added. After a further 5 hours, the mixture is worked up as described in Example 10. Demethylation and splitting off of the protective groups are carried out as described in Example 10, and the title compound is obtained as a colourless solid. Rf=0.33 (Running agent system A)

3''-N-Demethyl-3''-N-(β-n-butoxyethyl-sisomycin is obtained in an analogous manner, Rf=0.58 (Running agent system A).

EXAMPLE 13

3''-N-demethyl-3''-B-β-butenyl-sisomycin 400 mg of 1,2',3,6'-tetra-N-acetyl-sisomycin in 5 ml of methanol and 3 ml of water are stirred with 100 mg of crotonaldehyde at room temperature for 0.5 hour. After adding 100 mg of sodium cyanoboranate, the mixture is allowed to react at room temperature for 2 hours and then worked up as described in Example 10. (Rf=0.64, running agent system B). For oxidative demethylation, the product thus obtained is dissolved in 8 ml of H$_2$O and this solution is added to a solution of 320 mg of potassium hexacyanoferrate-III and 150 mg of sodium hydroxide in 8 ml of water, whilst stirring well. The mixture is left at room temperature for 48 hours and diluted with 40 ml of acetone, the salts which have precipitated are filtered off and the filtrate is evaporated in vacuo. For purification, the crude product thus obtained is filtered over a short silica gel column (eluting agent system B). 3''-N-Demethyl-3''-N-β-butenyl-1,2',3,6'-tetra-N-acetyl-sisomycin is thus obtained as an amorphous solid. $(\alpha)_D^{22} = +148°$ (c=1.0 CH$_3$OH), Rf=0.7 (running agent system B). The procedure for splitting off the acety groups is as described in Example 10, and the title compound is obtained as an amorphous solid. (Rf=0.36 (running agent system A).

In the same manner, oxidative desmethylation of 3''-N-tolylethyl-1,2',3,6'-tetra-N-acetyl-sisomycin gives 3''-N-demethyl-3''-N-tolylethyl-1,2',3,6'-tetra-N-acetyl-sisomycin with $(\alpha)_D^{22} = +134°$ (c=0.84 CH$_3$OH), and from this, by splitting off the protective groups 1. 3''-N-Demethyl-3''-N-tolylethyl-sisomycin Rf=0.45 (running agent system A) and 2. 3''-N-Demethyl-3''-N-allyl-sisomycin Rf=0.33 (running agent system A)

EXAMPLE 14

3''-N-Demethyl-3''-ethyl-sisomycin 12.5 g of 3''-N-ethyl-sisomycin are added to a solution of 16 g of cadmium carbonate hydrate in 120 ml of 25% strength aqueous ammonia and 400 ml of water. The mixture is cooled to 0° to −1° C. and treated within one hour with a solution of 18 g potassium hexacyano ferrate-III in 440 ml of water and stirring. After neutralisation with 20% strength aqueous sulfuric acid the precipitate is filtered off, the filtrate is chromatographed over a short column with a basic ion exchange agent (OH⁻-form, Lewatit MP 500 ® BAYER AG, Leverkusen). The extract is evaporated in vacuo, the residue is treated with methanol, methylenechloride and passed through a filter. After evaporation of the filtrate 10.0 g of the title compound are obtained as an amorphous solid.

$[\alpha]_D^{22} = +179°$ (c=1.0 H₂O)

What is claimed is:

1. A pseudotrisaccharide compound of the formula (I) or a pharmaceutically usable salt thereof

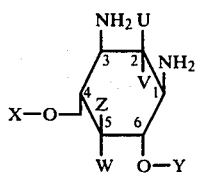

in which

X represents a radical of the formula

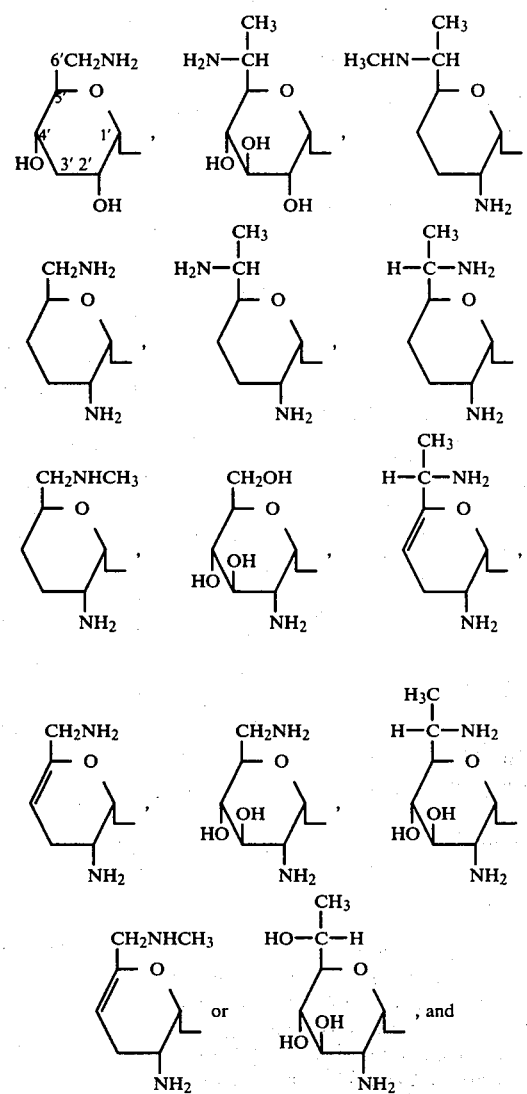

Y designates a radical of the formula

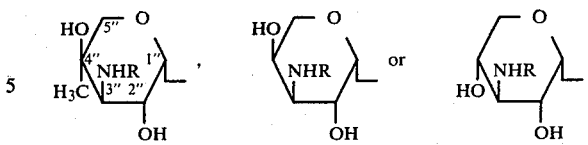

U and V are (a) both hydrogen or (b) one is hydrogen and the other is hydroxyl,

Z is hydrogen, hydroxyl or amino, and

W is hydrogen or hydroxyl with one of W and Z being hydrogen

R is alkyl having from 2 to 8 carbon atoms, alkenyl having from 2 to 6 carbon atoms, alkinyl having from 2 to 6 carbon atoms, cycloalkyl, cycloalkenyl having from 3 to 10 carbon atoms, cycloalkyl or cycloalkenyl-methyl or -ethyl, phenyl, naphthyl, phenylmethyl or phenylethyl, each of the hydrocarbon radicals being optionally substituted by from 1 to 3 substituents which are the same or different and each of which is hydroxyl, alkoxy having from 1 to 4 carbon atoms, alkylthio having from 1 to 4 carbon atoms, halogen, nitro, amino or monoalkylamino or dialkylamino having from 1 to 4 carbon atoms in the alkyl moiety in each case.

2. A compound according to claim 1, which are 3″—NR derivatives of the antibiotics gentamycin A, gentamycin B, gentamycin B₁, gentamycin C₁, gentamycin C₁ₐ, gentamycin C₂, gentamycin C₂ₐ, gentamycin C₂ᵦ, gentamycin X₂, sisomycin, JI-20A, JI-20B, verdamycin, G 52, G 418, 66-40 B, 66-40 D, mutamucin 1, mutamycin 2, mutamycin 4, mutamycin 5 and mutamycin 6.

3. 3″-N-Demethyl-3″-N-ethylsisomycin or a pharmaceutically usable salt thereof.

4. 3″-N-Demethyl-3″-N-propylsisomycin or a pharmaceutically usable salt thereof.

5. 3″-N-Demethyl-3″-N-n-butylsisomycin or a pharmaceutically usable salt thereof.

6. 3″-N-Demethyl-3″-N-pentylsisomycin or a pharmaceutically usable salt thereof.

7. 3″-N-Demethyl-3″-N-heptylsisomycin or a pharmaceutically usable salt thereof.

8. 3″-N-Demethyl-3″-N-(β-dimethylproply)-sisomycin or a pharmaceutically usable salt thereof.

9. 3″-N-Demethyl-3″-N-allylsisomycin or a pharmaceutically usable salt thereof.

10. 3″-N-Demethyl-3″-N-(β-butenyl)-sisomycin or a pharmaceutically usable salt thereof.

11. 3″-N-Demethyl-3″-N-tolyethylsisomycin or a pharmaceutically usable salt thereof.

12. 3″-N-Demethyl-3″-N-(β-aminoethyl)-sisomycin or a pharmaceutically usable salt thereof.

13. 3″-N-Demethyl-3″-N-(β-methoxyethyl)-sisomycin or a pharmaceutically usable salt thereof.

14. 3″-N-Demethyl-3″-N-(γ-methoxybutyl)-sisomycin or a pharmaceutically usable salt thereof.

15. 3″-N-Demethyl-3″-N-(γ,ε-dimethoxyhexyl)-sisomycin or a pharmaceutically usable salt thereof.

16. 3″-N-Demethyl-3″-N-(β-butoxyethyl)-sisomycin or a pharmaceutically usable salt thereof.

17. Compounds according to claim 1 which are sodium salts.

18. A process for the preparation of a compound according to claim 13 which comprises reacting a compound of the formula (III)

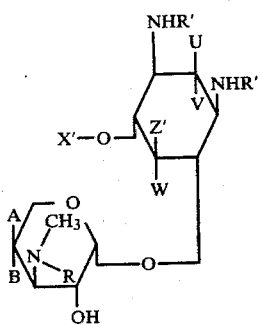

in which
- A is hydroxyl or hydrogen,
- B is hydroxyl, hydrogen or methyl,
- R, U, V and W have the same meaning as defined hereinbefore in claim 1 formula I,
- Z' is hydrogen, hydroxyl, amino or amino which is protected by an amino-protective group (R'), and
in which
- X' represents a radical of the formula

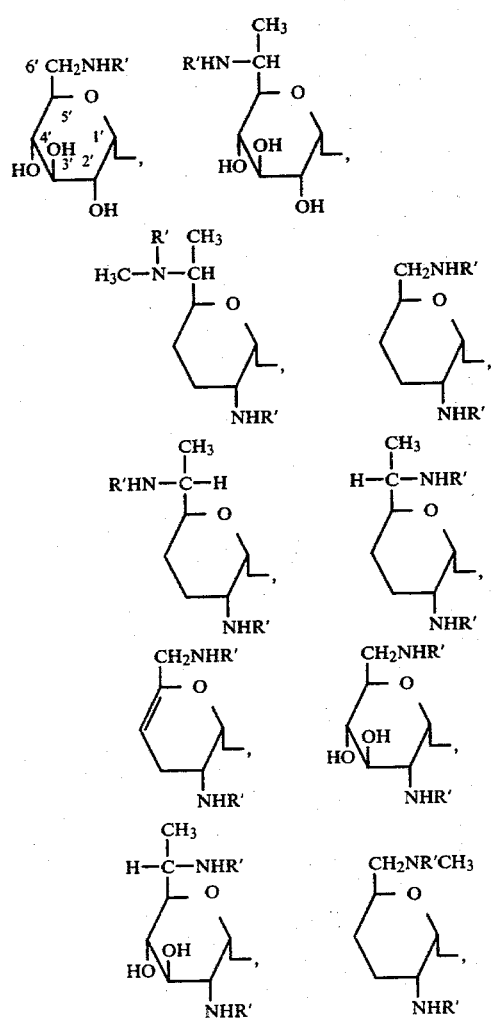

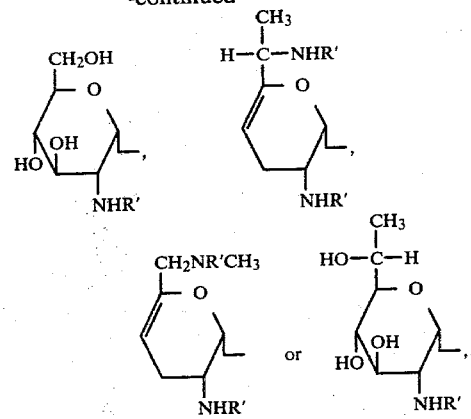

in which
R' is an amino-protective group, with an oxidizing agent, removing an amino-protective group when present, and isolating the pseudotrisaccharide of the formula (I) in the free form or in the form of an acid addition salt thereof.

19. A process according to claim 18 in which the reaction is carried out at from $-20°$ to $100°$ C.

20. A process according to claim 18 or claim 19 in which the reaction is carried out in the presence of an inert solvent.

21. A process according to claim 18 in which the oxidizing agent is a heavy metal salt, peroxide, halogen, halogen oxyacid or salt thereof, a nitrogen oxide or molecular oxygen.

22. A pharmaceutical composition containing as an active ingredient an antibacterially effective amount of a compound according to claim 1 in admixture with a solid, or liquid or liquefied gaseous diluent.

23. A pharmaceutical composition of claim 22 in the form of a sterile or physiologically isotonic aqueous solution.

24. A composition according to claim 22 or 23 containing from 0.5 to 95% by weight of the said active ingredient.

25. A medicament in dosage unit form comprising an antibacterially effective amount of a compound according to claim 1 together with an inert pharmaceutical carrier.

26. A medicament of claim 25 in the form of tablets, pills, dragees, capsules, ampoules, or suppositories.

27. A method of combating disease caused by bacteria in warm-blooded animals which comprises administering to the said animals an antibacterially effective amount of an active compound according to claim 1 either alone or in admixture with a diluent or in the form of a medicament.

28. A method according to claim 27 in which the active compound is administered in an amount of 0.4 to 40 mg per kg body weight per day.

29. A method according to claim 28 in which animals are ruminants.

30. A method according to any one of claims 27, 28 or 30 in which the active compound is administered orally.

31. A method according to claim 27 in which the active compound is administered topically.

32. A method according to claim 27 in which the active ingredient is administered parenterally.

* * * * *